US00RE46825E

(19) United States
(12) Reissued Patent
Heagle

(10) Patent Number: US RE46,825 E
(45) Date of Reissued Patent: May 8, 2018

(54) METHOD AND APPARATUS FOR BRIDGING FROM A DRESSING IN NEGATIVE PRESSURE WOUND THERAPY

(71) Applicant: Smith & Nephew, Inc., Memphis, TN (US)

(72) Inventor: David G. Heagle, Taunton, MA (US)

(73) Assignee: SMITH & NEPHEW, INC., Memphis, TN (US)

(21) Appl. No.: 14/261,296

(22) Filed: Apr. 24, 2014

Related U.S. Patent Documents

Reissue of:
(64) Patent No.: 8,162,907
Issued: Apr. 24, 2012
Appl. No.: 12/356,246
Filed: Jan. 20, 2009

(51) Int. Cl.
*A61M 1/00* (2006.01)
*A61M 27/00* (2006.01)
*A61F 13/02* (2006.01)
*A61F 13/00* (2006.01)

(52) U.S. Cl.
CPC ..... *A61M 27/00* (2013.01); *A61F 13/00068* (2013.01); *A61F 13/0203* (2013.01); *A61M 1/0086* (2014.02); *A61M 1/0088* (2013.01); *A61F 2013/0054* (2013.01); *A61F 2013/00174* (2013.01); *A61F 2013/00412* (2013.01);
(Continued)

(58) Field of Classification Search
CPC ..... A61M 1/0088; A61M 27/00
USPC ..... 604/313, 290, 304–307, 327, 540, 541, 604/543; 602/41–44
See application file for complete search history.

(56) References Cited

U.S. PATENT DOCUMENTS 3,367,332 A 2/1968 Groves
3,486,504 A 12/1969 Austin, Jr.
3,568,675 A 3/1971 Harvey
(Continued)

FOREIGN PATENT DOCUMENTS

AU 674837 B2 1/1997
DE 41 11 122 A1 4/1993
(Continued)

OTHER PUBLICATIONS

US 6,216,701, 04/2001, Heaton et al. (withdrawn)
(Continued)

*Primary Examiner* — Beverly M Flanagan
(74) *Attorney, Agent, or Firm* — Knobbe, Martens, Olson & Bear LLP

(57) ABSTRACT

A method of bridging from a wound dressing to a wound port for negative pressure wound therapy includes positioning an elongate wick between a wound and a remote location with respect to the wound. The elongate wick includes a three-dimensional spacer fabric having an upper fabric layer spaced from a lower fabric layer by an intermediate layer of pile threads. The elongate wick is covered with a flexible wick cover such that an enclosure is formed around the elongate wick. A substantially fluid-tight seal is established between a first end of the elongate wick cover and the wound dressing such that a reservoir is defined over the wound in which a negative pressure may be maintained. A substantially fluid-tight seal is established between a second end of the elongate wick cover and a fluid port configured for connection to a source of negative pressure.

40 Claims, 4 Drawing Sheets

(52) U.S. Cl.
CPC ..... *A61F 2013/00536* (2013.01); *A61F 2013/00553* (2013.01)

(56) References Cited

U.S. PATENT DOCUMENTS 3,572,340 A 3/1971 Lloyd et al.
3,712,298 A 1/1973 Snowdon et al.
3,809,086 A 5/1974 Schachet et al.
3,874,387 A 4/1975 Barbieri
4,080,970 A 3/1978 Miller
4,112,947 A 9/1978 Nehring
4,112,949 A 9/1978 Rosenthal et al.
4,136,696 A 1/1979 Nehring
4,266,545 A 5/1981 Moss
4,382,441 A 5/1983 Svedman
4,524,064 A 6/1985 Nambu
4,605,399 A 8/1986 Weston et al.
4,743,232 A 5/1988 Kruger
4,921,492 A 5/1990 Schultz et al.
4,969,880 A 11/1990 Zamierowski
4,990,137 A 2/1991 Graham
4,997,438 A 3/1991 Nipper
5,071,409 A 12/1991 Rosenberg
5,100,395 A 3/1992 Rosenberg
5,100,396 A 3/1992 Zamierowski
5,106,629 A 4/1992 Cartmell et al.
5,141,503 A 8/1992 Sewell, Jr.
5,149,331 A 9/1992 Ferdman et al.
5,152,757 A 10/1992 Eriksson
5,160,322 A 11/1992 Scheremet et al.
5,176,663 A 1/1993 Svedman et al.
5,178,157 A 1/1993 Fanlo
5,180,375 A * 1/1993 Feibus ..... 604/264
5,195,977 A 3/1993 Pollitt
5,261,893 A 11/1993 Zamierowski
5,263,922 A 11/1993 Sova et al.
5,437,683 A * 8/1995 Neumann et al. ..... 606/151
D364,679 S 11/1995 Heaton et al.
5,484,427 A 1/1996 Gibbons
5,527,293 A 6/1996 Zamierowski
5,536,233 A 7/1996 Khouri
5,549,584 A 8/1996 Gross
5,588,958 A 12/1996 Cunningham et al.
5,599,289 A 2/1997 Castellana
5,636,643 A 6/1997 Argenta et al.
5,645,081 A 7/1997 Argenta et al.
5,678,564 A 10/1997 Lawrence et al.
5,701,917 A 12/1997 Khouri
5,733,305 A 3/1998 Fleischmann
5,795,584 A 8/1998 Totakura et al.
5,840,049 A 11/1998 Tumey et al.
5,911,222 A 6/1999 Lawrence et al.
5,944,703 A 8/1999 Dixon et al.
6,010,524 A 1/2000 Fleischmann
6,071,267 A 6/2000 Zamierowski
6,117,111 A 9/2000 Fleischmann
6,135,116 A 10/2000 Vogel et al.
D434,150 S 11/2000 Tumey et al.
6,142,982 A 11/2000 Hunt et al.
6,174,306 B1 1/2001 Fleischmann
6,203,563 B1 3/2001 Fernandez
6,261,276 B1 7/2001 Reitsma
6,325,788 B1 12/2001 McKay
6,345,623 B1 2/2002 Heaton et al.
6,348,423 B1 2/2002 Griffiths et al.
6,398,767 B1 6/2002 Fleischmann
6,406,447 B1 6/2002 Thrash et al.
6,420,622 B1 7/2002 Johnston et al.
6,458,109 B1 10/2002 Henley et al.
6,488,643 B1 12/2002 Tumey et al.
6,500,112 B1 12/2002 Khouri
D469,175 S 1/2003 Hall et al.
D469,176 S 1/2003 Hall et al.
6,520,982 B1 2/2003 Boynton et al.
6,553,998 B2 4/2003 Heaton et al.
D475,134 S 5/2003 Randolph
6,557,704 B1 5/2003 Randolph
D478,659 S 8/2003 Hall et al.
6,607,495 B1 8/2003 Skalak et al.
6,626,891 B2 9/2003 Ohmstede
6,648,862 B2 11/2003 Watson
6,685,681 B2 2/2004 Lockwood et al.
6,695,823 B1 2/2004 Lina et al.
6,695,824 B2 2/2004 Howard et al.
D488,558 S 4/2004 Hall
6,752,794 B2 6/2004 Lockwood et al.
6,755,807 B2 6/2004 Risk, Jr. et al.
6,764,462 B2 7/2004 Risk, Jr. et al.
6,767,334 B1 7/2004 Randolph
6,800,074 B2 10/2004 Henley et al.
6,814,079 B2 11/2004 Heaton et al.
6,824,533 B2 11/2004 Risk, Jr. et al.
6,855,135 B2 2/2005 Lockwood et al.
6,856,821 B2 2/2005 Johnson
6,887,228 B2 5/2005 McKay
6,887,263 B2 5/2005 Bleam et al.
6,936,037 B2 8/2005 Bubb et al.
6,942,633 B2 9/2005 Odland
6,942,634 B2 9/2005 Odland
6,951,553 B2 10/2005 Bubb et al.
6,960,181 B2 11/2005 Stevens
6,979,324 B2 12/2005 Bybordi et al.
D515,701 S 2/2006 Horhota et al.
6,994,702 B1 2/2006 Johnson
7,004,915 B2 2/2006 Boynton et al.
7,022,113 B2 4/2006 Lockwood et al.
7,037,254 B2 5/2006 O'Connor et al.
7,052,167 B2 5/2006 Vanderschuit
7,070,584 B2 7/2006 Johnson et al.
7,077,832 B2 7/2006 Fleischmann
7,108,683 B2 * 9/2006 Zamierowski ..... 604/304
7,117,869 B2 10/2006 Heaton et al.
7,128,719 B2 10/2006 Rosenberg
7,128,735 B2 10/2006 Weston
7,144,390 B1 12/2006 Hannigan et al.
7,169,151 B1 1/2007 Lytinas
7,182,758 B2 2/2007 McCraw
7,195,624 B2 3/2007 Lockwood et al.
7,198,046 B1 4/2007 Argenta et al.
7,214,202 B1 5/2007 Vogel et al.
7,216,651 B2 5/2007 Argenta et al.
D544,092 S 6/2007 Lewis
7,273,054 B2 9/2007 Heaton et al.
7,276,051 B1 10/2007 Henley et al.
7,279,612 B1 10/2007 Heaton et al.
7,316,672 B1 1/2008 Hunt et al.
D565,177 S 3/2008 Locke et al.
7,338,482 B2 3/2008 Lockwood et al.
7,351,250 B2 4/2008 Zamierowski
7,361,184 B2 4/2008 Joshi
7,381,211 B2 6/2008 Zamierowski
7,381,859 B2 6/2008 Hunt et al.
7,396,345 B2 7/2008 Knighton et al.
7,410,495 B2 8/2008 Zamierowski
7,413,570 B2 8/2008 Zamierowski
7,413,571 B2 8/2008 Zamierowski
7,422,576 B2 9/2008 Boynton et al.
7,438,705 B2 10/2008 Karpowicz et al.
7,485,112 B2 2/2009 Karpowicz et al.
7,503,910 B2 3/2009 Adahan
7,531,711 B2 5/2009 Sigurjonsson et al.
7,534,927 B2 5/2009 Lockwood et al.
7,569,742 B2 8/2009 Haggstrom et al.
7,625,362 B2 12/2009 Boehringer et al.
7,645,269 B2 1/2010 Zamierowski
7,651,484 B2 1/2010 Heaton et al.
7,670,323 B2 3/2010 Hunt et al.
7,678,102 B1 3/2010 Heaton
7,686,785 B2 3/2010 Boehringer et al.
7,794,438 B2 9/2010 Henley et al.
7,838,717 B2 * 11/2010 Haggstrom et al. ..... 602/53
7,862,718 B2 1/2011 Doyen et al.
7,880,050 B2 2/2011 Robinson et al.
7,942,866 B2 * 5/2011 Radl et al. ..... 604/543

(56) References Cited

U.S. PATENT DOCUMENTS

| | | | | |
|---|---|---|---|---|
| 8,021,347 | B2 | 9/2011 | Vitaris et al. | |
| 8,083,712 | B2 | 12/2011 | Biggie et al. | |
| 8,133,211 | B2 | 3/2012 | Cavanaugh, II et al. | |
| 8,142,419 | B2 | 3/2012 | Heaton et al. | |
| 8,147,468 | B2 | 4/2012 | Barta et al. | |
| 8,148,595 | B2 | 4/2012 | Robinson et al. | |
| 8,152,785 | B2 | 4/2012 | Vitaris | |
| 8,158,844 | B2 | 4/2012 | McNeil | |
| 8,162,907 | B2 | 4/2012 | Heagle | |
| 8,168,848 | B2 | 5/2012 | Lockwood et al. | |
| 8,188,331 | B2 | 5/2012 | Barta et al. | |
| 8,202,261 | B2 | 6/2012 | Kazala, Jr. et al. | |
| 8,241,261 | B2 | 8/2012 | Randolph et al. | |
| 8,246,606 | B2 | 8/2012 | Stevenson et al. | |
| 8,257,327 | B2 | 9/2012 | Blott et al. | |
| 8,267,908 | B2 | 9/2012 | Coulthard | |
| 8,298,200 | B2 | 10/2012 | Vess et al. | |
| 8,376,972 | B2 | 2/2013 | Fleischmann | |
| 8,382,731 | B2 | 2/2013 | Johannison | |
| 8,469,915 | B2 | 6/2013 | Johannison et al. | |
| 8,506,554 | B2 | 8/2013 | Adahan | |
| 8,545,466 | B2 * | 10/2013 | Andresen et al. | 604/319 |
| 8,734,410 | B2 | 5/2014 | Hall et al. | |
| 9,017,302 | B2 | 4/2015 | Vitaris et al. | |
| 9,033,942 | B2 | 5/2015 | Vess | |
| 9,227,000 | B2 | 1/2016 | Fink et al. | |
| 9,474,654 | B2 | 10/2016 | Heagle et al. | |
| 2001/0020145 | A1 | 9/2001 | Satterfield et al. | |
| 2001/0031943 | A1 | 10/2001 | Urie | |
| 2001/0043943 | A1 | 11/2001 | Coffey | |
| 2002/0016577 | A1 | 2/2002 | Ohmstede | |
| 2002/0143286 | A1 | 10/2002 | Tumey | |
| 2002/0151836 | A1 | 10/2002 | Burden | |
| 2003/0093041 | A1 | 5/2003 | Risk, Jr. et al. | |
| 2003/0208149 | A1 | 11/2003 | Coffey | |
| 2003/0212357 | A1 | 11/2003 | Pace | |
| 2003/0212359 | A1 | 11/2003 | Butler | |
| 2003/0219469 | A1 | 11/2003 | Johnson et al. | |
| 2004/0006319 | A1 | 1/2004 | Lina et al. | |
| 2004/0030304 | A1 | 2/2004 | Hunt et al. | |
| 2004/0039415 | A1 | 2/2004 | Zamierowski | |
| 2004/0064132 | A1 | 4/2004 | Boehringer et al. | |
| 2004/0073151 | A1 | 4/2004 | Weston | |
| 2004/0093026 | A1 | 5/2004 | Weidenhagen et al. | |
| 2004/0122434 | A1 | 6/2004 | Argenta et al. | |
| 2004/0193218 | A1 | 9/2004 | Butler | |
| 2004/0241213 | A1 | 12/2004 | Bray | |
| 2004/0243073 | A1 | 12/2004 | Lockwood et al. | |
| 2005/0010153 | A1 | 1/2005 | Lockwood et al. | |
| 2005/0020955 | A1 | 1/2005 | Sanders et al. | |
| 2005/0070835 | A1 | 3/2005 | Joshi | |
| 2005/0070858 | A1 | 3/2005 | Lockwood et al. | |
| 2005/0085795 | A1 | 4/2005 | Lockwood et al. | |
| 2005/0101940 | A1 * | 5/2005 | Radl et al. | 604/543 |
| 2005/0177190 | A1 | 8/2005 | Zamierowski | |
| 2005/0182445 | A1 | 8/2005 | Zamierowski | |
| 2005/0222527 | A1 | 10/2005 | Miller et al. | |
| 2005/0222544 | A1 | 10/2005 | Weston | |
| 2005/0261642 | A1 | 11/2005 | Weston | |
| 2005/0261643 | A1 | 11/2005 | Bybordi et al. | |
| 2006/0015087 | A1 | 1/2006 | Risk, Jr. et al. | |
| 2006/0025727 | A1 | 2/2006 | Boehringer et al. | |
| 2006/0039742 | A1 | 2/2006 | Cable, Jr. et al. | |
| 2006/0041247 | A1 | 2/2006 | Petrosenko et al. | |
| 2006/0079852 | A1 | 4/2006 | Bubb et al. | |
| 2006/0100586 | A1 | 5/2006 | Karpowicz et al. | |
| 2006/0100594 | A1 | 5/2006 | Adams et al. | |
| 2006/0116620 | A1 | 6/2006 | Oyaski | |
| 2007/0014837 | A1 | 1/2007 | Johnson et al. | |
| 2007/0021697 | A1 | 1/2007 | Ginther et al. | |
| 2007/0027414 | A1 | 2/2007 | Hoffman et al. | |
| 2007/0032754 | A1 | 2/2007 | Walsh | |
| 2007/0032755 | A1 | 2/2007 | Walsh | |
| 2007/0032778 | A1 | 2/2007 | Heaton et al. | |
| 2007/0055209 | A1 | 3/2007 | Patel et al. | |
| 2007/0066946 | A1 | 3/2007 | Haggstrom et al. | |
| 2007/0078366 | A1 | 4/2007 | Haggstrom et al. | |
| 2008/0082035 | A1 * | 4/2008 | Evans | 602/60 |
| 2008/0167593 | A1 * | 7/2008 | Fleischmann | 602/48 |
| 2008/0195017 | A1 * | 8/2008 | Robinson et al. | 602/44 |
| 2009/0012501 | A1 | 1/2009 | Boehringer et al. | |
| 2009/0124988 | A1 | 5/2009 | Coulthard | |
| 2009/0126103 | A1 | 5/2009 | Dietrich et al. | |
| 2009/0131892 | A1 | 5/2009 | Karpowicz et al. | |
| 2009/0157016 | A1 | 6/2009 | Carmeli | |
| 2009/0227968 | A1 | 9/2009 | Vess | |
| 2009/0227969 | A1 * | 9/2009 | Jaeb | A61M 1/0088 604/313 |
| 2009/0234307 | A1 | 9/2009 | Vitaris | |
| 2009/0264837 | A1 | 10/2009 | Adahan | |
| 2009/0293887 | A1 | 12/2009 | Wilkes et al. | |
| 2009/0299249 | A1 | 12/2009 | Wilkes et al. | |
| 2009/0299255 | A1 | 12/2009 | Kazala, Jr. et al. | |
| 2009/0299256 | A1 | 12/2009 | Barta et al. | |
| 2009/0299257 | A1 | 12/2009 | Long et al. | |
| 2009/0299303 | A1 | 12/2009 | Seegert | |
| 2009/0299307 | A1 | 12/2009 | Barta et al. | |
| 2009/0299308 | A1 | 12/2009 | Kazala et al. | |
| 2009/0299340 | A1 | 12/2009 | Kazala et al. | |
| 2009/0299341 | A1 | 12/2009 | Kazala et al. | |
| 2009/0299342 | A1 | 12/2009 | Cavanaugh, II et al. | |
| 2009/0312728 | A1 | 12/2009 | Randolph et al. | |
| 2010/0069850 | A1 | 3/2010 | Fabo | |
| 2010/0069885 | A1 | 3/2010 | Stevenson et al. | |
| 2010/0160901 | A1 | 6/2010 | Hu et al. | |
| 2011/0125113 | A1 | 5/2011 | Adahan | |
| 2011/0130712 | A1 | 6/2011 | Topaz | |
| 2012/0302976 | A1 | 11/2012 | Locke et al. | |
| 2015/0073358 | A1 | 3/2015 | Jaeb et al. | |

FOREIGN PATENT DOCUMENTS

| | | |
|---|---|---|
| DE | 295 04 378 U1 | 10/1995 |
| DE | 43 06 478 A1 | 12/2008 |
| EP | 0 020 662 B1 | 7/1984 |
| EP | 0 358 302 | 3/1990 |
| EP | 0 392 640 B1 | 6/1995 |
| EP | 0 441 418 B1 | 7/1995 |
| EP | 0 777 504 B1 | 10/1998 |
| EP | 1 169 071 A1 | 1/2002 |
| EP | 0 751 757 B1 | 2/2002 |
| EP | 0 853 950 B1 | 10/2002 |
| EP | 1 487 389 A1 | 12/2004 |
| EP | 0 982 015 B1 | 8/2006 |
| EP | 1 905 465 B1 | 1/2010 |
| EP | 2 319 550 | 5/2011 |
| EP | 1 578 477 B1 | 9/2011 |
| EP | 2 413 858 | 2/2012 |
| EP | 1 660 000 B1 | 10/2012 |
| EP | 2 545 946 A3 | 3/2013 |
| EP | 2 490 637 B1 | 1/2014 |
| EP | 2 051 675 B1 | 6/2014 |
| GB | 1 549 756 | 3/1977 |
| GB | 2 195 255 A | 4/1988 |
| GB | 2 235 877 A | 3/1991 |
| GB | 2 307 180 B | 6/2000 |
| GB | 2 336 546 B | 6/2000 |
| GB | 2 344 531 A | 6/2000 |
| SU | 1762940 | 1/1989 |
| WO | WO 80/01139 | 6/1980 |
| WO | WO 80/02182 | 10/1980 |
| WO | WO 84/01904 | 5/1984 |
| WO | WO 89/05133 | 6/1989 |
| WO | WO 90/11795 | 10/1991 |
| WO | WO 92/19313 | 11/1992 |
| WO | WO 96/05873 | 2/1996 |
| WO | WO 03/057307 | 7/2003 |
| WO | WO 03/101508 | 12/2003 |
| WO | WO 2005/009488 | 2/2005 |
| WO | WO 2005/016179 | 2/2005 |
| WO | WO 2005/061025 | 7/2005 |
| WO | WO 2006/015599 | 2/2006 |
| WO | WO 2007/006306 | 1/2007 |
| WO | WO 2007/016590 | 2/2007 |

(56) References Cited

FOREIGN PATENT DOCUMENTS

| | | |
|---|---|---|
| WO | WO 2007/019038 | 2/2007 |
| WO | WO 2007/041642 | 4/2007 |
| WO | WO 2007/085396 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2008/008032 | 1/2008 |
| WO | WO 2008/012278 | 1/2008 |
| WO | WO 2008/027449 | 3/2008 |
| WO | WO 2008/043067 | 4/2008 |
| WO | WO 2008/100440 | 8/2008 |
| WO | WO 2008/100446 | 8/2008 |
| WO | WO 2008/131895 | 11/2008 |
| WO | WO 2008/135997 | 11/2008 |
| WO | WO 2008/141470 | 11/2008 |
| WO | WO 2009/068665 | 6/2009 |
| WO | WO 2009/086580 | 7/2009 |
| WO | WO 2009/088925 | 7/2009 |
| WO | WO 2009/111655 | 9/2009 |
| WO | WO 2009/137194 | 11/2009 |
| WO | WO 2009/140376 | 11/2009 |
| WO | WO 2009/141820 | 11/2009 |
| WO | WO 2009/145894 | 12/2009 |
| WO | WO 2010/014177 | 2/2010 |
| WO | WO 2010/033769 | 3/2010 |
| WO | WO 2010/042240 | 4/2010 |
| WO | WO 2010/051073 | 5/2010 |
| WO | WO 2010/059730 | 5/2010 |
| WO | WO 2010/078166 | 7/2010 |

OTHER PUBLICATIONS

US 7,186,244, 03/2007, Hunt et al. (withdrawn)

B. M. Kostiuchenok, et al., "The Vacuum Effect in the Surgical Treatment of Purulent Wounds," Russian Journal: Vestnik Khirurgii, Sep. 1986 (18-21).

Y.N. Usupov, et al., "Active Wound Drainage," Russian Journal: Vestnik Khirugii, Apr. 1987 (42-45).

N.A. Bagautdinov (Kazan), "Variant of External Vacuum Aspiration in the Treatment of Purulent Diseases of Soft Tissues," UDC 616-002.36 (94-96).

Yu A. Davydov, et al., "Bacteriological and Cytological Assessment of Vacuum Therapy of Purulent Wounds", Vestnik Khirurgii, Oct. 1988 (48-52).

Göran Sandén, M.D., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Arnljots, et al., "Irrigation Treatment in Split-thickness Skin Grafting of Intractable Leg Ulcers," Scand J Plast Reconstr Surg 19: 211-213, 1985.

Bagautdinov, N.A., "Variant of External Vacuum Aspiration in the Treatment of Purulent Diseases of Soft Tissues," in Current Problems in Modern Clinical Surgery: Interdepartmental Collection, edited by V. Ye. Volkov et al. (Chuvashia State University, Cheboksary, USSR 1986) pp. 94-96 (with English translation).

European Examination Report, re EPO Application No. 09839009. 9, dated Oct. 12, 2016.

Meyer, MD., et al., "In Surgery, Medicine and the Specialties A Manual of its Practical Application", Bier's Hyperemic Treatment, Second Revised Edition, W.B. Saunders Company, 1909.

Sandén, Göran MD., et al., "Staphylococcal Wound Infection in the Pig: Part II. Innoculation, Quantification of Bacteria, and Reproducibility," Annals of Plastic Surgery, vol. 23, No. 3, Sep. 1989, (219-223).

Jeter, Katherine F., et al., "Managing Draining Wounds and Fistulae: New and Established Methods", Chronic Wound Care, 1990, pp. 240-246.

Chariker, M. E. et al. (eds), "Effective Management of Incisional and Cutaneous Fistulae with Closed Suction Wound Drainage," Contemporary Surgery, vol. 34, Jun. 1989, pp. 59-63.

Yu A. Davydov, et al., "Concepts for Clinical Biological Management of the Wound Process in the Treatment of Purulent Wounds Using Vacuum Therapy," Vestnik Khirugii, Feb. 1991, 132-135).

Chardack, et al., "Experimental studies on Synthetic Substitutes for Skin and Their Use in the Treatment of Burns," vol. 155, No. 1 (128-136).

Gorica Zivadinovic, et al., "Vacuum Therapy in the Treatment of Peripheral Blood Vessels," Conference Papers of the 5th Timok Medical Days, Majdanpek, 1986 (161-164).

Ryosuke Fujimoro, M.D., et al., "Sponge Fixation Method for Treatment of Early Scars," From the Department of Dermatology in the Faculty Medicine, Kyoto University, vol. 42, No. 4, Oct. 1968 (323-326).

W. Fleischmann, et al., Vacuum Sealing: Indication, Technique and Results, Emr J Orthop Surg Tramatol (1995) 5:37-40.

Sherry Stoll, "Energetic Remedies—Cupping: Healing Within a Vacuum," https://www.suite101.com/article.cfm/energetic)remedies/74531, Apr. 13, 2005.

Mulder, G.D, et al., "Clinicians' Pocket Guide to Chronic Wound Repair," Wound Healing Publications Second Edition, 1991.

Yu A. Davydov, et al., "Vacuum Therapy in the Treatment of Purulent Lactation Mastitis," Russian Journal: Vesnik Khirurgii, Sep. 1986 (66-70).

W. Fleischmann, "Vacuum Sealing for Treatment of Problematical Wounds", University Surgical Clinic and Polyclinic—Accident Surgery Department, WundForum Spezial—IHW 94.

Björn, et al., "Irrigation Treatment in Split-thickness Skin Grafting of Intractable Leg Ulcers," Scand J Plast Reconstr Surg 19: 211-213, 1985.

Paul Svedman, et al., "Staphylococcal Wound Infection in the Pig: Part I. Course," Annals of Plastic Surgery, vol. 23, No. 3, Sep. 1989 (212-218).

Paul Svedman, "A Dressing Allowing Continuous Treatment of a Biosurface," IRCS Medical Science: Biomedical Technology; Clinical Medicine; Surgery and Transplantation, 7, 221 (1979).

Paul Svedman, "Irrigation Treatment of Leg Ulcers," The Lancet, Sep. 3, 1983 (532-534).

H. Teder, et al., "Continuous Wound Irrigation in the Pig," Journal of Investigative Surgery, vol. 3 (399-407).

P. Svedman, "A Dressing System Providing Fluid Supply and Suction Drainage Used for Continuous or Intermittent Irrigation," Annals of Plastic Surgery, vol. 17, No. 2, Aug. 1986 (125-133).

Yu A. Davydov, et al., "Vacuum Therapy in treatment of Acute Purulent Diseases of Soft Tissues and Purulent Wounds," Vestnik Khirurgii, (Surgeon's Herald), Medicine Publishers, 1986.

International Search Report Application No. PCT/US09/046987 dated Aug. 6, 2009.

* cited by examiner

METHOD AND APPARATUS FOR BRIDGING FROM A DRESSING IN NEGATIVE PRESSURE WOUND THERAPY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND

1. Technical Field

The present disclosure relates generally to treating a wound with negative or reduced pressure. In particular, the disclosure relates to a dressing for transporting fluids from a wound site to a fluid port in a remote location, and also a method for applying the dressing.

2. Background of Related Art

Various techniques to promote healing of a wound involve providing suction to the wound. For example, a vacuum source may serve to carry wound exudates away from the wound, which may otherwise harbor bacteria that inhibit the body's natural healing process. One particular technique for promoting the body's natural healing process may be described as negative pressure wound therapy (NPWT). This technique involves the application of a reduced pressure, e.g. sub-atmospheric, to a localized reservoir over a wound. Sub-atmospheric pressure has been found to assist in closing the wound by promoting blood flow to the area, thereby stimulating the formation of granulation tissue and the migration of healthy tissue over the wound. This technique has proven effective for chronic or non-healing wounds, but has also been used for other purposes such as post-operative wound care.

The general NPWT protocol provides for covering the wound with a flexible cover layer such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most NPWT treatments apply a reduced pressure using an external vacuum source. Fluid communication must therefore be established between the reservoir and the vacuum source. To this end, a fluid port is often coupled to the cover layer to provide an interface for a fluid conduit extending from the external vacuum source. The fluid port typically exhibits a degree of rigidity, which provides for a convenient reception of the fluid conduit. The fluid port also may project somewhat from the surrounding skin, and may thus tend to cause discomfort for patients as the fluid port is inadvertently pressed into the wound. This tendency is particularly evident when a fluid port is used on wounds on a patient's back, heel or other locations where pressure points develop as the patient reclines or sits. Accordingly, it may be advantageous to position the fluid port at a location remote from the wound, and to draw fluid from the wound to the remotely positioned fluid port.

SUMMARY

A method of bridging from a wound dressing to a wound port for negative pressure wound therapy includes positioning an elongate wick between a wound and a remote location with respect to the wound wherein the elongate wick includes a three-dimensional spacer fabric. The three-dimensional spacer fabric defines an upper fabric layer and a lower fabric layer, wherein the upper fabric layer and the lower fabric layer are spaced from one another by an intermediate layer of pile threads. The elongate wick is covered with a flexible wick cover such that an enclosure is formed around the elongate wick. A substantially fluid-tight seal is established between a first end of the elongate wick cover and the wound dressing such that a reservoir is defined over the wound in which a negative pressure may be maintained. A substantially fluid-tight seal is established between a second end of the elongate wick cover and at least one of a fluid port, a fluid conduit and a source of negative pressure.

The method may also include positioning a skin covering between the wound and the remote location to substantially minimize contact of fluids with a skin surface adjacent the wound. The elongate skin covering may define a width of about 2 inches, the elongate wick may define a width of about 1 inch, and the wick cover may define a width of about 3 inches.

The method may also include the step of applying heat to the spacer fabric to conform the spacer fabric to a particular body contour. Also, the method may include the step of drawing fluids through the elongate wick.

According to another aspect of the disclosure, a composite wound dressing apparatus includes a cover layer for defining a reservoir over a wound in which a negative pressure may be maintained by forming a substantially fluid-tight seal around the wound. The cover layer includes an aperture therein through which fluids may be extracted from the reservoir. An elongate wick includes a first end in fluid communication with the reservoir through the aperture in the cover layer, and a second end disposed remotely with respect to the aperture in the cover layer. The elongate wick includes a three-dimensional spacer fabric. A flexible wick cover extends over the elongate wick. The wick cover has a first end configured for forming a substantially fluid tight seal over the aperture in the cover layer, and a second end including an aperture therein through which fluids may be extracted from the elongate wick. A fluid port is coupled to the wick cover and in fluid communication with the second end of the elongate wick through the aperture in the wick cover.

The apparatus may include a skin covering positioned beneath at least a portion of the elongate wick to substantially minimize contact of fluids with a skin surface adjacent the wound. The skin covering may define a first width, the wick cover may define a second width and the elongate wick may define a third width, wherein the third width of the wick cover is substantially greater than the first width of the skin covering. The first width may be about 2 inches, the second width may be about one inch, and the third width may be about 3 inches.

The fluid port may be configured to receive a fluid conduit, and may include a flange coupled to an underside of the wick cover. The elongate wick may be treated with an antimicrobial agent, and the antimicrobial agent may be polyhexamethylene biguanide.

According to another aspect of the disclosure, a negative pressure wound therapy apparatus includes a cover layer for defining a reservoir over a wound in which a negative pressure may be maintained by forming a substantially fluid-tight seal around the wound. The cover layer includes an aperture therein through which fluids may be extracted from the reservoir. The apparatus also includes an elongate wick having a first end and a second end, wherein the first end is in fluid communication with the reservoir through the aperture in the cover layer, and the second end is disposed remotely with respect to the aperture in the cover layer. The elongate wick includes a three-dimensional spacer fabric. Also, a flexible wick cover extends over the elongate wick and has a first end and a second end. The first end of the wick cover is configured for forming a substantially fluid tight seal over the aperture in the cover layer, and the second end includes an aperture through which fluids may be extracted from the elongate wick. A vacuum source is in fluid communication with the reservoir, and is suitable for generating the negative pressure in the reservoir.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF EMBODIMENTS

Figure 1A:
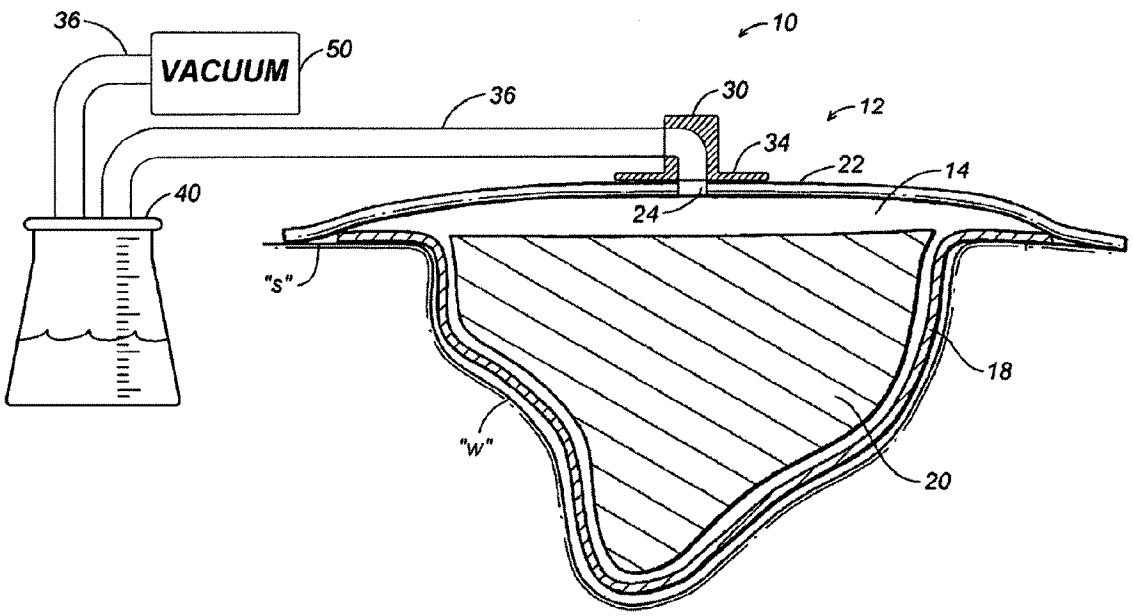
FIG. 1A is a cross sectional view of an NPWT treatment apparatus including a fluid port in the vicinity of a vacuum reservoir for treating a wound.
Figure 1B:
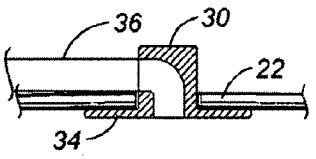
FIG. 1B is a partial cross sectional view of the fluid port of FIG. 1A affixed in an alternate configuration.

Referring initially to FIG. 1, an NPWT apparatus is depicted generally as 10 for use on a wound "w" surrounded by healthy skin "s." The NPWT apparatus 10 includes a wound dressing 12 positioned relative to the wound "w" to define a reservoir 14 in which a negative pressure appropriate to stimulate healing may be maintained.

Wound dressing 12 includes a contact layer 18 positioned in direct contact with the bed of wound "w" and may be formed from perforated film material. An appropriate perforated material permits the negative pressure applied to the reservoir to penetrate into the wound "w," and also permits exudates to be drawn through the contact layer 18. Passage of wound fluid through the contact layer 18 is preferably unidirectional such that exudates do not flow back into the wound bed. Unidirectional flow may be encouraged by conical or directional apertures formed in the contact layer 18, or a lamination of materials having absorption properties differing from those of contact layer 18. A non-adherent material may be selected such that contact layer 18 does not tend to cling to the wound "w" or surrounding tissue when it is removed. One exemplary material that may be used as a contact layer 18 is sold under the trademark XEROFORM®, CURITY®, and VENTEX® by Tyco Healthcare Group LP (d/b/a Covidien).

Wound filler 20 is positioned in the wound "w" over the contact layer 18 and is intended to allow wound dressing 12 to absorb, capture and/or wick wound exudates. Wound filler 20 is cut to a shape that is conformable to the shape of wound "w," and may be packed up to the level of healthy skin "s," or alternatively, wound filler 20 may overfill the wound "w." An absorbent material such as non-woven gauze, reticulated foam, or alginate fibers may be used for filler 20 to transfer any exudate that migrates through contact layer 18 away from the wound "w". An antimicrobial dressing sold under the trademark KERLIX® AMD by Tyco Healthcare Group LP (d/b/a Covidien), may be suitable for use as filler 20.

Wound dressing 12 also includes a cover layer 22. Cover layer 22 may be positioned over the wound "w" to form a substantially fluid-tight seal with the surrounding skin "s." Thus, cover layer 22 may act as both a microbial barrier to prevent contaminants from entering the wound "w," and also a fluid barrier maintaining the integrity of vacuum reservoir 14. Cover layer 22 is preferably formed from a moisture vapor permeable membrane to promote the exchange of oxygen and moisture between the wound "w" and the atmosphere, and is preferably transparent permit a visual assessment of wound conditions without requiring removal of the cover layer 22. A membrane that provides a sufficient moisture vapor transmission rate (MVTR) is a transparent membrane sold under the trade name POLYSKIN® II by Tyco Healthcare Group LP (d/b/a Covidien). Cover layer 22 includes an aperture 24 therein, through which wound fluids and atmospheric gasses may be removed from the dressing 12 under the influence of a reduced pressure.

Figure 1C:
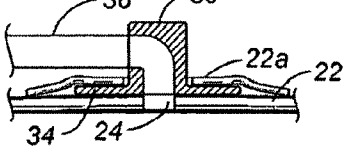
FIG. 1C is a partial cross sectional view of the fluid port of FIG. 1A affixed in another alternate configuration.

A fluid port 30 having a flange 34 may also be included in wound dressing 12 to facilitate connection of the wound dressing 12 to fluid conduit 36. The fluid port 30 may be configured as a rigid or flexible, low-profile component, and may be adapted to receive a fluid conduit 36 in a releasable and fluid-tight manner. An adhesive on the underside of flange 34 may provide a mechanism for affixing the fluid port 30 to the dressing 12, or alternatively the flange 34 may be positioned within reservoir 14 (FIG. 1B) such that an adhesive on an upper side of the flange 34 affixes the fluid port 30. As depicted in FIG. 1C, an additional alternative for affixing the fluid port to the cover layer involves securing the flange 34 to the cover layer with a skirt 22a. The skirt 22a may be constructed of an adhesively coated polymeric film similar to the cover layer 22. However it is affixed to the dressing, a hollow interior of the fluid port 30 provides fluid communication between the fluid conduit 36 and the reservoir 14.

Fluid conduit 36 extends from the fluid port 30 to provide fluid communication between the reservoir 14 and collection canister 40. Any suitable conduit may be used for fluid conduit 36 including those fabricated from flexible elastomeric or polymeric materials. Fluid conduit 36 may connect components of the NPWT apparatus by conventional air-tight means such as friction fit, bayonet coupling, or barbed connectors. The conduit connections may be made permanent, or alternatively a quick-disconnect or other releasable means may be used to provide some adjustment flexibility to the apparatus 10.

Collection canister 40 may comprise any container suitable for containing wound fluids. For example, a rigid bottle may be used as shown or alternatively a flexible polymeric pouch may be appropriate. Collection canister 40 may contain an absorbent material to consolidate or contain the wound drainage or debris. For example, super absorbent polymers (SAP), silica gel, sodium polyacrylate, potassium polyacrylamide or related compounds may be provided within canister 40. At least a portion of canister 40 may be transparent to assist in evaluating the color, quality or quantity of wound exudates. A transparent canister may thus assist in determining the remaining capacity of the canister or when the canister should be replaced.

Leading from collection canister 40 is another section of fluid conduit 36 providing fluid communication with vacuum source 50. Vacuum source 50 generates or otherwise provides a negative pressure to the NPWT apparatus 10. Vacuum source 50 may comprise a peristaltic pump, a diaphragmatic pump or other mechanism that draws fluids, e.g. atmospheric gasses and wound exudates, from the reservoir 14 appropriate to stimulate healing of the wound "w." Preferably, the vacuum source 50 is adapted to produce a sub-atmospheric pressure in the reservoir 14 ranging between about 20 mmHg and about 500 mm Hg, about 75 mm Hg to about 125 mm Hg, or, more preferably, between about 40 mm HG and 80 mm Hg.

Figure 2A:
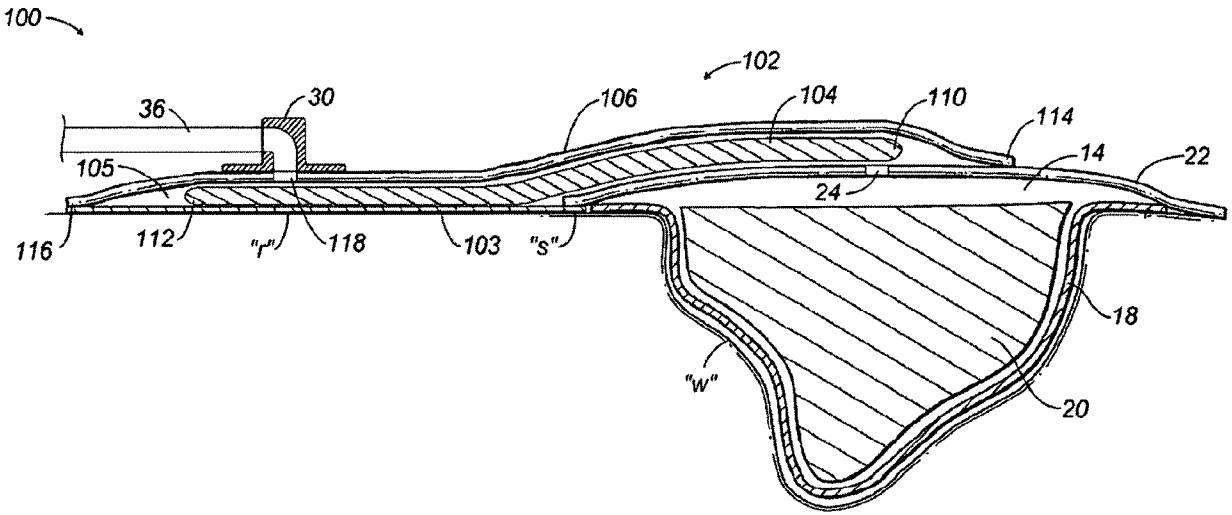
FIG. 2A is a cross sectional view of a composite wound dressing and bridging dressing with the fluid port in a remote location in accordance with the present disclosure as applied on the wound.
Figure 2B:
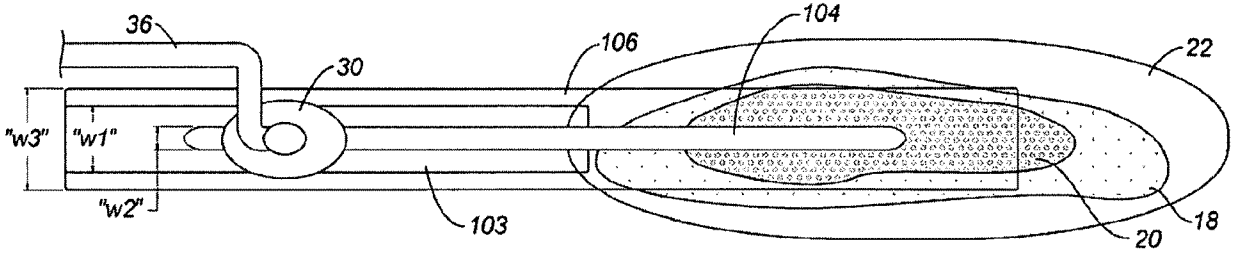
FIG. 2B is a top view of the composite dressing and bridging dressing of FIG. 2A.

Referring now to FIGS. 2A and 2B, a composite wound dressing 100 is depicted, which permits a fluid port 30 and the associated fluid conduit 36 to be located remotely with respect to the wound "w." Composite wound dressing 100 includes a contact layer 18, a wound filler 20 and a cover layer 22 applied to the wound "w" in a manner similar to wound dressing 12 discussed above with reference to FIG. 1. The fluid port 30, however, is affixed to the composite wound dressing 100 at a location "r" that is remote from the wound "w," rather than being affixed to the cover layer 22 at the aperture 24.

To provide fluid communication, or a "bridge," between aperture 24 and the remote location "r," a bridging dressing 102 is positioned partially over the cover layer 22 and partially over the healthy skin "s" to span the distance between the wound "w" and the remote location "r." The remote location "r" may be an area of the healthy skin "s" where the fluid port 30 or the associated fluid conduit 36 will tend not to irritate the wound "w" or to cause discomfort for the patient. If the wound "w" is located on the back of a patient, the remote location "r" may be, for example, at the chest or shoulder of the patient. This permits the patient to lie comfortably without placing undue pressure on the fluid port 30. To provide this functionality, a bridging dressing 102 may exhibit a length in the range from about 4 inches to about 12 inches, or more.

The bridging dressing 102 includes a skin covering such as film or lining 103, an elongate wick 104, a wick cover 106, and the fluid port 30. The film or lining 103 will be placed in contact with skin, typically, the healthy skin along a portion of the "bridge." The lining or film 103 may be any suitable film adapted for patient contact, and may or may not have an adhesive backing for securement to the skin. The film or lining 103 may overlap a peripheral portion of the cover 22. The film or lining 103 may or may not be adhesively coated, and, in some embodiments is a thin, transparent, polymeric membrane such as polyurethane, elastomeric polyester or polyethylene.

The film or lining 103 may serve to impede direct contact between the elongate wick 104 and the healthy skin "s." The film or lining 103 may exhibit a first width "w1" between two elongate edges that is substantially greater than a second width "w2" defined by the elongate wick 104. For instance, a lining 103 having a first width "w1" of about 2 inches may provide a sufficient area to permit an elongate wick 104 having a second width "w2" of about 1 inch to rest entirely within the confines of the lining 103. The film or lining 103 may be applied to the skin "s" either prior to the application of the elongate wick 104 and the wick cover 106, or concurrently therewith.

The elongate wick 104 defines a longitudinal direction therealong between a first end 110 positioned near the aperture 24 in the cover layer 22, and a second end 112 near the remote location "r." The elongate wick 104 is adapted for longitudinal transport of fluids therethrough. The elongate wick 104 may promote capillary action in a longitudinal direction to provide for the longitudinal transport of fluids. A cross section of individual fibers, or an arrangement of fibers may serve to transport fluids longitudinally. The elongate wick 104 may be constructed from materials suitable for use as wound filler 20. The elongate wick 104 may, for example, be constructed of hydrophobic fibers, such as continuous synthetic fibers, arranged as an elongate rope or cord. The fibers may be crimped, bulked or lofted to influence the absorptive, wicking or comfort characteristics of the elongate wick 104. U.S. Provisional Application No. 61/188,370, filed Aug. 8, 2008, the entire content of which is hereby incorporated by reference, describes various such processes and arrangements for fibers, which may be employed to construct the elongate wick 104 or the filler 20.

Figure 3:
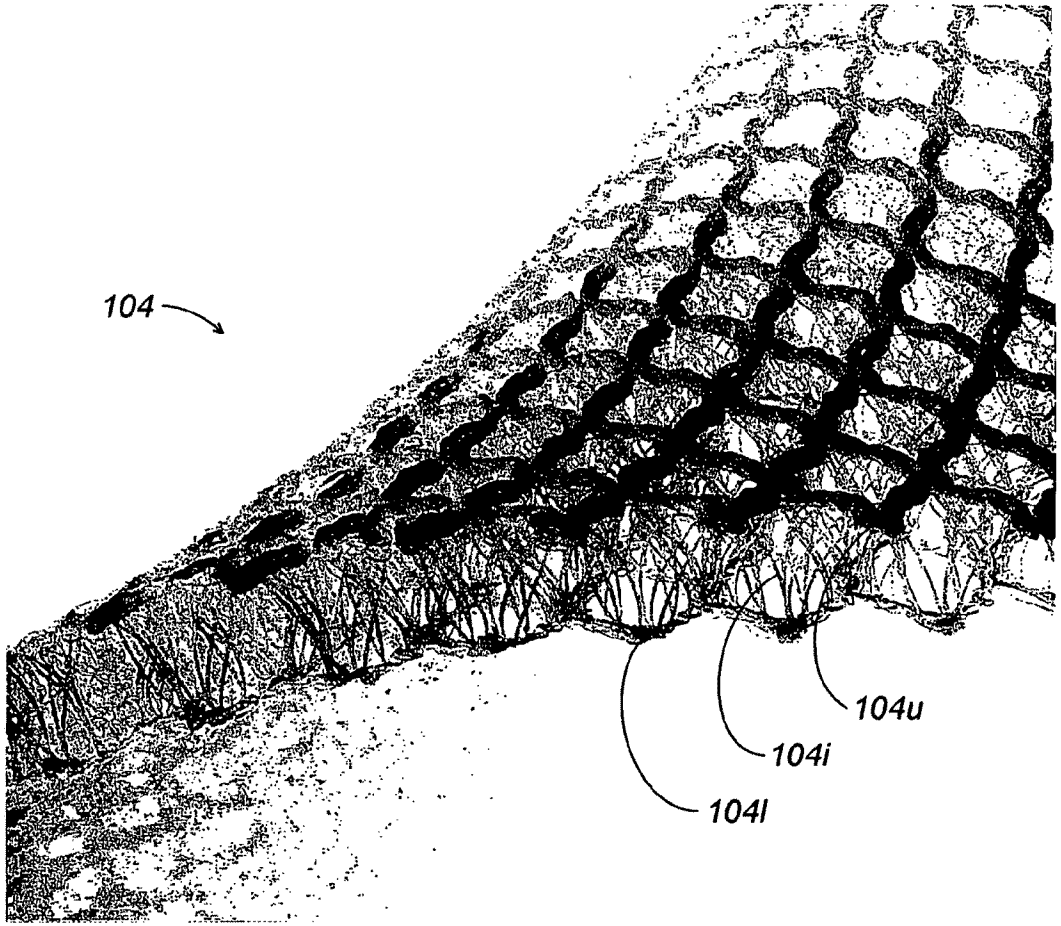
FIG. 3 is a close up perspective view of the elongate wick of FIG. 2A.

The elongate wick 104 may also be constructed from a three-dimensional spacer fabric. As depicted in FIG. 3, a three dimensional spacer fabric includes an upper fabric layer 104u spaced from a lower fabric layer 104l by an intermediate layer 104i of upright pile threads. The intermediate layer 104i of upright pile threads provides space between the upper and lower layers 104u and 104i through which wound fluids and atmospheric gasses may be transported.

This multi-layer arrangement offers a structural versatility, which permits the elongate wick 104 to conform to the needs of a particular patient or wound. The upright pile threads may exhibit a variety of different constructions in terms of surface structure, elasticity, diameter, length, position, number and orientation. For example, the upright pile threads may be arranged at a steep angle to provide cushioning in the event the upper and lower layers 104u and 104l are compressed together. Also, the upper and lower layers 104u and 104i may assume any particular weave or knit pattern. A ribbed knit pattern may provide flexibility in an appropriate direction to permit the wick to conform to highly contoured body areas. A variety of thicknesses, densities, compression, air permeability and softness characteristics may be provided by selecting an appropriate material and arrangement of the individual layers 104u, 104i and 104u.

An appropriate three-dimensional spacer fabric for use in elongate wick 104 is marketed under the trade name AirX—Comfort, by Tytex, Inc. of Woonsocket, R.I. In addition to offering a high MVTR and friction resistance, this product may be constructed to include a visco-elastic plastic yielding a heat-moldable structure. A heat-moldable wick 104 may be subjected to heat prior to positioning the wick 104 over lining 103 or healthy skin "s" to pre-conform the wick 104 to a particular body contour. Alternatively, visco-elastic plastics may be provided that are responsive to body heat to provide a conformable wick 104.

Alternatively, elongate wick 104 may be constructed from staple fibers, and may be arranged as woven or kitted fabrics. The fibers may be treated with antibacterial agents such as polyhexamethylene biguanide (PHMB) to decrease the incidence of infection, or other medicaments to promote healing of the wound "w." The fibers may also include combinations of materials or chemicals to tailor the wick for specific fluid transport, comfort or other specific requirements.

The wick cover 106 has a first end 114 positioned near the aperture 24 in the cover layer and beyond the first end 110 of the elongate wick 104. A second end 116 of the wick cover 106 is positioned near the remote location "r." The first end 114 of wick cover 106 forms a substantially fluid-tight seal with the cover layer 22, and the second end 116 of the wick cover 106 forms a substantially fluid tight seal with the lining 103 or the skin in the absence of the lining 103. The second end 114 of wick cover 106 may contact or be secured to lining 103 thereby assisting in securement of the lining relative to the subject and optionally forming an enclosure 105 between the wick cover 106 and the lining 103 substantially enclosing the a portion of the elongated wick 103 preventing exudate from contacting the skin. In the absence of a lining 103, an enclosure may be formed between the wick cover 106 and the skin "s."

Wick cover 106 may be constructed from any of the materials used to fabricate cover layer 22. For example, wick cover 106 may be constructed of an adhesively coated, thin, transparent, polymeric membrane such as polyurethane, elastomeric polyester or polyethylene. The thickness of the wick cover 106 may, for example, be in the range of about 0.8 mils to about 1.2 mils. Thicknesses in this range may permit wick cover 106 to conform comfortably to the contours of a patient's skin surrounding the elongate wick 104, and accommodate evacuation cycles associated with an NPWT procedure. The adhesive coating should provide firm, continuous adhesion to the lining 103, the skin "s" and/or the cover layer 22 such that leak paths are not readily formed as reservoir 14 is subjected to the evacuation cycles of an NPWT treatment. As seen in FIG. 2B, wick cover 106 may also define a third width "w3," which is substantially greater than the first width "w1" of the lining 103. This permits wick cover 106 to be adhesively secured to the skin "s" on either side of the elongate edges of the lining 103, and to an upper surface of the lining 103 as well. The adhesive should also not unduly interfere with the MVTR of the wick cover, and should peel away from the skin "s" easily when the wick cover 106 is no longer required.

An aperture 118 in the wick cover 106 facilitates fluid communication between fluid port 30 and the elongate wick 104. The fluid port 30 forms a substantially fluid tight seal with the wick cover 106 near the aperture 118 and receives fluid conduit 36. Fluid conduit 36 may be coupled to a vacuum source 50 as described above with reference to FIG. 1.

In this manner, fluids such as wound exudates and atmospheric gasses may be drawn from the reservoir 14, through the aperture 24 in the cover layer 22, and into the first end 110 of the elongate wick 104. The fluids are transported longitudinally through the wick 104 under the influence of the reduced pressure and the fluid transport properties of the wick 104 to the second end 112 of the wick 104 near the remote location "r." The fluids may then be removed from the bridging dressing 102 through the fluid port 30. Since the wick 104 and the wick cover 106 are generally more flexible and conformable to the contours of the patient's body, and also to the movements of the patient than fluid port 30, these components of bridging dressing 102 are typically more comfortable positioned adjacent to the wound "w."

Figure 4B:
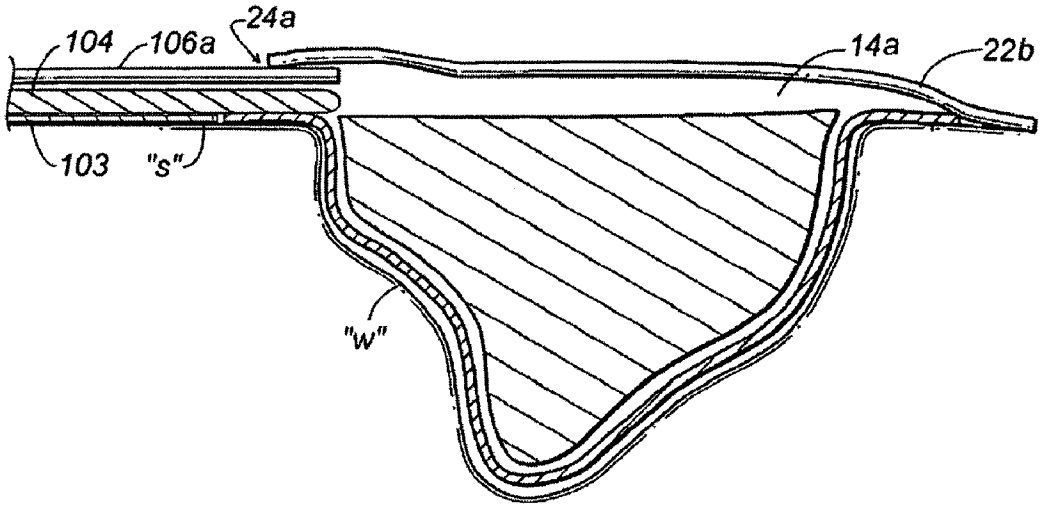
FIG. 4B is a partial cross sectional view of a bridging dressing coupled to a wound dressing in an alternate configuration.
Figure 4A:
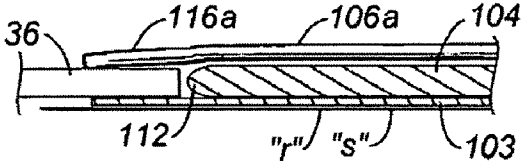
FIG. 4A is a partial cross-sectional view of an alternate configuration of a bridging dressing applied without a flanged fluid port.

Referring now to FIG. 4A, an alternate embodiment of the disclosure permits fluid communication between the fluid conduit 36 and the second end 112 of the wick 104 near the remote location "r" to be established without the use of a flanged fluid port. A wick cover 106a includes a second end 116a devoid of an aperture for the attachment of a fluid port. Rather, the wick cover 106a forms a substantially fluid tight seal with the fluid conduit 36 and the lining 103 surrounding the remote location "r." This configuration allows fluid conduit 36 to be placed comfortably at the remote location "r" rather than near the wound "w." Since the fluid conduit 36 may be generally less conformable or more rigid than the wick 104 and the wick cover 106a, placement of the fluid conduit 36 remote from the wound "w" may be more comfortable than adjacent the wound "w."

Referring now to FIG. 4B, another alternate embodiment of the disclosure permits fluid communication between the elongate wick 104 and a reservoir 104a over the wound "w." The wick cover 106a includes a first end 114a extending into the reservoir 14a. Cover layer 22b may form a substantially fluid-tight seal with an upper surface of the wick cover 106a such that an aperture 24a in the wick cover 106a permits fluid communication between the reservoir 14a and the elongate wick 104. This configuration permits application of the lining 103, the wick 104 and the wick cover 106a prior to the application of the cover layer 22b. Various other configurations of similar components may also provide a bridge for a wound dressing.

Although the foregoing disclosure has been described in some detail by way of illustration and example, for purposes of clarity or understanding, it will be obvious that certain changes and modifications may be practiced within the scope of the appended claims.

What is claimed is:

1. A composite wound dressing apparatus comprising:

a cover layer for defining a reservoir over a wound in which a negative pressure may be maintained by forming a substantially fluid-tight seal around the wound, the cover layer including an aperture therein through which fluids may be extracted from the reservoir;

an elongate wick having a first end and a second end, *wherein* the first end *is configured to be* in fluid communication with the reservoir through the aperture in the cover layer, *and* the second end *is configured to be* disposed remotely with respect to the aperture in the cover layer[, the elongate wick comprising a three-dimensional spacer fabric] *such that the elongate wick only partially extends over the cover layer and a portion of the elongate wick is not above the cover layer*;

a flexible wick cover extending over the elongate wick and *configured for extending partially over the cover layer, the wick cover* having a first end *configured to be positioned over the aperture in the cover layer* and a second end *configured to be disposed at a location remote from the wound and the cover layer such that the wick cover and the cover layer do not have substantially similar dimensions*, *the wick cover extending between the first end configured to be positioned over the aperture in the cover layer and the second end configured to be disposed at the location remote from the wound,* the first end of the wick cover configured for forming a substantially fluid tight seal over the aperture in the cover layer, the second end of the wick cover [cover] including an aperture therein through which fluids may be extracted from the elongate wick, the wick cover having an adhesive coating [for] *along a length of the wick cover extending between the first and second ends, the adhesive coating for* establishing [a] *the* substantially fluid tight seal over the aperture in the cover layer and with [the] *a* skin surface [disposed remotely] *at the location remote* from the wound *cover*; and a fluid port coupled to the wick cover and in fluid communication with the second end of the elongate wick through the aperture in the wick cover.

2. The apparatus according to claim 1, further comprising a skin covering positioned beneath at least a portion of the elongate wick to impede direct contact of the elongate wick with the skin surface.

3. The apparatus according to claim 2, wherein the skin covering defines a first width, the elongate wick defines a second width and the wick cover defines a third width, the third width of the wick cover substantially greater than the first width of the skin covering.

4. The apparatus according to claim 3, wherein the first width is about 2 inches, the second width is about one inch, and the third width is about 3 inches.

5. The apparatus according to claim 1, wherein the fluid port is configured to receive a fluid conduit.

6. The apparatus according to claim 2, wherein the fluid port includes a flange coupled to an underside of the wick cover.

7. The apparatus according to claim 1, wherein the elongate wick is treated with an antimicrobial agent.

8. The apparatus according to claim 7, wherein the antimicrobial agent is polyhexamethylene biguanide.

9. A negative pressure wound therapy apparatus, comprising:

a cover layer [disposed over] *for defining* a reservoir [in] *over* a wound in which a negative pressure may be maintained;

an elongate wick having a first end and a second end, *wherein* the first end *is configured to be* in fluid communication with the reservoir, *and* the second end *is configured to be at a location* disposed remotely from the wound[, the elongate wick comprising a three-dimensional spacer fabric] *such that the elongate wick only partially extends over the cover layer and a portion of the elongate wick is not above the cover layer*;

a wick cover disposed over the elongate wick and *configured for extending partially over the cover layer, the wick cover* having a first end *configured to be positioned over an aperture in the cover layer* and a second end *configured to be disposed at the location disposed remotely from the wound and the cover layer such that the wick cover and the cover layer do not have substantially similar dimensions, the wick cover extending between the first end configured to be positioned over the aperture in the cover layer and the second end configured to be disposed at the location remote from the wound cover,* the first end of the wick cover configured for forming a substantially fluid tight seal [with] *over the aperture in* the cover layer, the second end of the wick cover including an aperture in fluid communication with the elongate wick, an adhesive coating [for the wick cover to establish a] *provided along a length of the wick cover, the adhesive coating for establishing the* substantially fluid tight seal over the aperture in the cover layer and with [the] *a* skin surface *at the location* disposed remotely from the wound; and a vacuum source *configured to be* in fluid communication with the reservoir.

10. The apparatus according to claim 1, including a vacuum source in fluid communication with the fluid port, the vacuum source suitable for generating the negative pressure in the reservoir.

11. The apparatus according to claim 9 wherein the vacuum source is in fluid communication with the reservoir through the elongate wick.

12. The apparatus according to claim 11 including a fluid port mounted to the wick cover, and wherein the vacuum source is in fluid communication with the reservoir through the fluid port.

13. The apparatus according to claim 11 wherein the elongate wick comprises polyhexamethylene biguanide.

14. The apparatus according to claim 11 wherein the *elongate wick comprises a* three dimensional spacer fabric [comprises] *comprising* an upper fabric layer, a lower fabric layer, and an intermediate layer of pile threads between the upper fabric layer and the lower fabric layer.

15. The apparatus according to claim 11 wherein the elongate wick comprises hydrophobic fibers.

16. The apparatus according to claim 2, wherein at least a portion of the skin covering is interposed between the skin surface and the wick cover.

*17. A negative pressure wound therapy apparatus comprising:*

*a main wound dressing portion comprising a cover layer for defining a vacuum reservoir over a wound in which negative pressure may be maintained; and*

*a bridging dressing portion configured to provide fluid communication between the vacuum reservoir and a remote location from the main wound dressing portion, the bridging dressing portion comprising:*

*a lower film layer having a first width between two elongate edges of the lower film layer;*

*an elongate wick having a second width between two elongate edges of the elongate wick, the elongate wick configured to be positioned over the lower film layer and having a length that spans a distance between the main wound dressing portion and the remote location, wherein the elongate wick is configured to be in fluid communication with the vacuum reservoir of the main wound dressing portion; and*

*an upper film layer having a third width between two elongate edges of the upper film layer, the upper film layer configured to be positioned over the elongate wick and configured to be partially over the cover layer of the main wound dressing portion;*

*wherein the second width is less than a width of the main dressing portion;*

*wherein the elongate wick is in contact with the upper film layer and the lower film layer along an entire length of the elongate wick; and*

*wherein at least one of the upper film layer and the lower film layer has an adhesive coating provided thereon at the remote location and establishing a substantially fluid tight seal with a skin surface disposed at the remote location from the main wound dressing portion.*

*18. The apparatus according to claim 17, wherein the cover layer includes an aperture therein through which negative pressure may be applied to the vacuum reservoir.*

*19. The apparatus according to claim 18, wherein the bridging dressing portion is positioned partially over the cover layer.*

*20. The apparatus according to claim 19, wherein the upper film layer has an adhesive coating for establishing a substantially fluid tight seal over the aperture in the cover layer.*

*21. The apparatus according to claim 17, wherein the main wound dressing portion comprises a contact layer configured to be positioned over the wound and a filler between the contact layer and the cover layer.*

*22. The apparatus according to claim 17, further comprising a fluid port coupled to the upper film layer.*

*23. The apparatus according to claim 17, wherein the elongate wick comprises a three-dimensional spacer fabric.*

*24. The apparatus according to claim 17, wherein the upper film layer is secured to the lower film layer forming an enclosure between the upper film layer and the lower film layer substantially enclosing the elongate wick.*

*25. The apparatus according to claim 17, wherein the second width is less than the first width or the third width.*

*26. The apparatus according to claim 17, wherein the cover layer of the main portion and the upper film layer of the bridging portion comprise the same material.*

*27. A negative pressure wound therapy apparatus comprising:*

*a wound dressing comprising a cover layer having an aperture; and*

*an elongate bridge having a first end and a second end, the first end configured to be positioned over the aperture in the wound dressing and the second end configured to be disposed at a remote location away from the wound dressing, wherein the elongate bridge comprises:*

*an upper film layer,*

*an elongate wick comprising a three-dimensional fabric material positioned beneath the upper film layer, the elongate wick configured to be positioned over the aperture in the wound dressing at the first end of the elongate bridge; and*

*a lower film layer positioned beneath the elongate wick and secured to the upper film layer;*

*wherein at least the elongate wick extends from the aperture in the wound dressing to the remote location;*

*wherein the elongate wick is in contact with the upper film layer and the lower film layer along an entire length of the elongate wick;*

*wherein the first end of the elongate bridge is provided with an adhesive coating configured to establish a substantially fluid tight seal over the aperture in the wound dressing and that adheres the first end of the elongate bridge to the cover layer; and*

*wherein the lower film layer has an adhesive coating for establishing a substantially fluid tight seal with a skin surface disposed remotely from the wound dressing.*

*28. The apparatus according to claim 27, wherein the lower film layer is secured to the upper film layer forming an enclosure between the upper film layer and the lower film layer substantially enclosing the elongate wick.*

*29. The apparatus according to claim 27, wherein the three-dimensional spacer fabric comprises:*

*a lower fabric layer;*

*an intermediate layer of upright pile threads; and*

*an upper fabric layer spaced from the lower fabric layer by the intermediate layer of upright pile threads.*

*30. The apparatus according to claim 29, wherein one or both of the lower fabric layer and the upper fabric layer comprises a knit or weave pattern.*

*31. The apparatus according to claim 27, wherein the elongate wick comprises hydrophobic fibers.*

*32. The apparatus according to claim 27, wherein the elongate wick comprises a plurality of fibers that are crimped, bulked or lofted.*

*33. The apparatus according to claim 27, wherein the lower film layer has a first width, the elongate wick has a second width, and the upper film layer has a third width, wherein the second width is less than the first width or the third width.*

*34. The apparatus according to claim 27, further comprising a fluid port at the second end of the elongate bridge for removal of fluids from the elongate bridge.*

*35. The apparatus according to claim 34, further comprising an aperture in the upper film layer, wherein the fluid port is sealed to the upper film layer over the aperture in the upper film layer.*

*36. The apparatus according to claim 27, wherein the wound dressing comprises a contact layer and a filler positioned between the contact layer and the cover layer.*

*37. The apparatus according to claim 27, further comprising a fluid conduit for connecting the second end of the elongate bridge to a vacuum source.*

*38. The apparatus according to claim 27, further comprising a vacuum source configured to apply vacuum to the elongate bridge.*

*39. The apparatus according to claim 27, further comprising a collection canister for containing wound fluids removed from a wound through the elongate bridge.*

*40. The apparatus according to claim 1, wherein the elongate wick comprises a three dimensional spacer fabric.*

* * * * *